US012560563B2

(12) United States Patent
De Kort et al.

(10) Patent No.: US 12,560,563 B2
(45) Date of Patent: Feb. 24, 2026

(54) CALIBRATING DIRECT FLOW SIMULATIONS OF ROCK SAMPLES

(71) Applicant: SHELL OIL COMPANY, Houston, TX (US)

(72) Inventors: Daan Willem De Kort, Amsterdam (NL); Matthias Appel, Houston, TX (US); Benjamin Charles Anger, Houston, TX (US); John Justin Freeman, Houston, TX (US); Faruk Ömer Alpak, Houston, TX (US); Lynn Faith Gladden, Cambridge (GB); Andrew John Sederman, Cambridge (GB); Michael David Mantle, Cambridge (GB); Kaspars Karlsons, Cambridge (GB)

(73) Assignee: SHELL USA, INC., Houston, TX (US)

( * ) Notice: Subject to any disclaimer, the term of this patent is extended or adjusted under 35 U.S.C. 154(b) by 364 days.

(21) Appl. No.: 18/248,467

(22) PCT Filed: Nov. 2, 2021

(86) PCT No.: PCT/US2021/057707
§ 371 (c)(1),
(2) Date: Apr. 10, 2023

(87) PCT Pub. No.: WO2022/098645
PCT Pub. Date: May 12, 2022

(65) Prior Publication Data
US 2023/0408431 A1 Dec. 21, 2023

Related U.S. Application Data

(60) Provisional application No. 63/111,133, filed on Nov. 9, 2020, provisional application No. 63/109,074, filed on Nov. 3, 2020.

(51) Int. Cl.
*G01N 24/08* (2006.01)
*G01N 23/046* (2018.01)
(Continued)

(52) U.S. Cl.
CPC ......... *G01N 24/081* (2013.01); *G01N 23/046* (2013.01); *G01N 23/083* (2013.01); *G01N 33/241* (2013.01)

(58) Field of Classification Search
CPC .. G01N 24/081; G01N 23/046; G01N 23/083; G01N 33/241; G01N 15/0826; G01N 2015/0846; G01N 15/088
See application file for complete search history.

(56) References Cited

U.S. PATENT DOCUMENTS 7,894,891 B2 * 2/2011 Song ..................... A61B 5/055
600/546
10,222,441 B2 * 3/2019 Kaditz ............... G01R 33/5608
(Continued)

OTHER PUBLICATIONS

International Search Report and Written Opinion Received for PCT Patent Application No. PCT/US2021/057707, Mailed on Feb. 2, 2022, 9 Pages.
(Continued)

*Primary Examiner* — Tung S Lau
(74) *Attorney, Agent, or Firm* — SHELL USA, INC.

(57) ABSTRACT

A method for calibrating a direct flow simulation of a rock sample involves providing a 3D image of a rock sample and generating a segmented structural image of the rock sample from the 3D image by selecting voxels to represent either a pore space or a solid material. Fluid flow is simulated on the segmented structural image with a direct flow simulation. A 3D spatially-resolved fluid velocity map is generated for one or more fluid phases at a pore-scale resolution using pulsed field gradient nuclear magnetic resonance imaging. The simulated fluid flow and the 3D spatially-resolved fluid
(Continued)

velocity map are compared to calibrate the direct flow simulation across the rock sample.

15 Claims, 9 Drawing Sheets

(51) Int. Cl.
   G01N 23/083        (2018.01)
   G01N 33/24         (2006.01)

(56)                    References Cited

U.S. PATENT DOCUMENTS

| | | | |
|---|---|---|---|
| 10,234,372 B2 * | 3/2019 | Li | G01N 24/08 |
| 10,301,924 B2 * | 5/2019 | Utsuzawa | E21B 47/00 |
| 2005/0010383 A1 | 1/2005 | Le Ravalec-Dupin et al. | |
| 2007/0238969 A1 * | 10/2007 | Song | A61B 5/4504 |
| | | | 600/410 |
| 2011/0060572 A1 | 3/2011 | Brown et al. | |
| 2012/0126811 A1 * | 5/2012 | Subbarao | G01R 33/445 |
| | | | 324/309 |
| 2016/0139291 A1 * | 5/2016 | Saidian | G01N 24/081 |
| | | | 324/303 |
| 2017/0032532 A1 | 2/2017 | Andersen et al. | |
| 2017/0152730 A1 | 6/2017 | Modavi et al. | |
| 2017/0223947 A1 | 8/2017 | Gall et al. | |
| 2018/0003786 A1 * | 1/2018 | Washburn | G01N 23/04 |
| 2023/0342517 A1 * | 10/2023 | Mansor | E21B 41/00 |

OTHER PUBLICATIONS

De Kort et al., "Acquisition of Spatially-Resolved Displacement Propagators Using Compressed Sensing Apgste-Rare MRI" Journal of Magnetic Resonance, Jul. 14, 2018, vol. 295, 39 Pages.

Chen et al., "Lattice Boltzmann Method for Fluid Flows", Annual Review of Fluid Mechanics, 1998, vol. 30, pp. 329-364.

Alpak et al., "Prediction of Fluid Topology and Relative Permeability in Imbibition in Sandstone Rock by Direct Numerical Simulation", Advances in Water Resources, Dec. 2018, vol. 122, 26 Pages.

Alpak et al.,"Direct Simulation of Pore-scale Two-phase Viscocapillary Flow on Large Digital Rock Images Using a Phase-field Lattice Boltzmann Method on General-purpose Graphics Processing Units", Computational Geosciences, Jul. 22, 2019, vol. 23, pp. 849-880.

De Kort et al., "Under-sampling and Compressed Sensing of 3d Spatially-resolved Displacement Propagators in Porous Media Using Apgste-Rare MRI", Magnetic Resonance Imaging, 2019, vol. 56, pp. 24-31.

Karlsons et al., "Identification of Sampling Patterns for High-resolution Compressed Sensing MRI of Porous Materials: 'Learning' From X-ray Microcomputed Tomography Data", Journal of Microscopy, 2019, vol. 276, Issue 2, pp. 63-81.

Otsu, "A Threshold Selection Method From Gray-level Histograms", IEEE Transactions on Systems, Man, and Cybernetics, Jan. 1979, vol. SMC-9, No. 1, pp. 62-66.

Andra et al., "Digital Rock Physics Benchmarks—Part II: Computing Effective Properties", Computers and Geosciences, vol. 50, Jan. 2013, pp. 33-43.

Saxena et al., "Effect of Image Segmentation & Voxel Size on Micro-CT Computed Effective Transport & Elastic Properties", Marine and Petroleum Geology, Sep. 1, 2017, vol. 86, pp. 972-990.

Chuang et al., "Fuzzy C-means Clustering With Spatial Information for Image Segmentation", Computerized Medical Imaging and Graphics, 2006, vol. 30, Issue No. 1, pp. 9-15.

Beucher et al. "The Morphological Approach to Segmentation: The Watershed Transformation", Mathematical Morphology in Image Processing, Chapter 12, Jan. 1993, pp. 433-481.

Benning et al. "Phase Reconstruction From Velocity-encoded MRI Measurements—A Survey of Sparsity-promoting Variational Approaches" Journal of Magnetic Resonance, 2014, vol. 238, pp. 26-43.

Lustig et al. "Sparse MRI: The Application of Compressed Sensing for Rapid MR Imaging" Magnetic Resonance in Medicine, 2007, vol. 58, pp. 1182-1195.

Cotts et al. "Pulsed Field Gradient Stimulated Echo Methods for Improved Nmr Diffusion Measurements in Heterogeneous Systems" Journal of Magnetic Resonance, 1989, vol. 83, pp. 252-266.

Duchon "Lanczos Filtering in One and Two Dimensions" Journal of Applied Meteorology and Climatology, 1979, vol. 18, pp. 1016-1022.

Pluim et al., Mutual-information-based Registration of Medical Images: a Survey, IEEE Transactions on Medical Imaging, Aug. 2003, vol. 22, Issue No. 8, pp. 986-1004.

Studholme et al., "An Overlap Invariant Entropy Measure of 3d Medical Image Alignment", Pattern Recognition, 1999, vol. 32, Issue 1, pp. 71-86.

Manz et al.,"Flow and Dispersion in Porous Media: Lattice-boltzmann and Nmr Studies" AIche Journal, Sep. 1999, vol. 45, Issue No. 9, pp. 1845-1854.

Saxena et al., "Rock Properties From Micro-CT Images: Digital Rock Transforms for Resolution, Pore Volume and Field of View", Advances in Water Resources, 2019, vol. 134, 13 Pages.

Saxena et al., "Estimating Pore Volume of Rocks From Pore-scale Imaging", Transport in Porous Media, 2019, vol. 129, pp. 403-412.

Zambrano et al., "Fluid Flow Simulation and Permeability Computation in Deformed Porous Carbonate Grainstones", Advances in Water Resources, 2018, vol. 115, pp. 95-111.

Hertel et al., "Fast Spatially-resolved T2 Measurements With Constant-gradient CPMG", Magnetic Resonance Imaging, 2019, vol. 56, pp. 70-76.

Yang et al., "Direct Numerical Simulation of Pore-scale Flow in a Bead Pack: Comparison With Magnetic Resonance Imaging Observations", Advances in Water Resources, 2013, vol. 54, pp. 228-241.

Shukla et al., "Accurate Phase-shift Velocimetry in Rock", Journal of Magnetic Resonance, 2016, vol. 267, pp. 43-53.

Romanenko et al., Velocity Field Measurements in Sedimentary Rock Cores by Magnetization Prepared 3D Sprite, Journal of Magnetic Resonance, 2012, vol. 223, pp. 120-128.

Valvatne et al., "Predictive Pore-scale Modeling of Two-phase Flow in Mixed Wet Media", Water Resources Research, 2004, vol. No. 40, pp. 1-21.

Hussain et al., "Monitoring Water Transport in Sandstone Using Flow Propagators: A Quantitative Comparison of Nuclear Magnetic Resonance Measurement With Lattice Boltzmann and Pore Network Simulations", Advances in Water Resources, 2013, vol. No. 60, pp. 64-74.

Øren et al., "Extending Predictive Capabilities to Network Models", SPE Journal, 1997, pp. 369-381.

Search Report Received for European Application No. 21889909.4 Mailed on Dec. 2, 2024, 15 Pages (15 Pages of Official Copy).

* cited by examiner

30

4.5 mm

Z
Y — X

30

4.5 mm

Z
Y — X

HIGH

μCT IMAGE INTENSITY [A.U.]

LOW

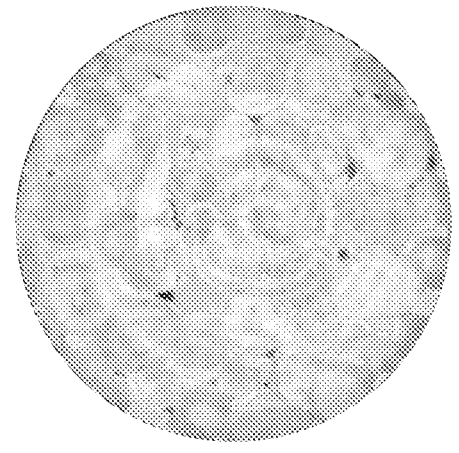
FIG. 6A
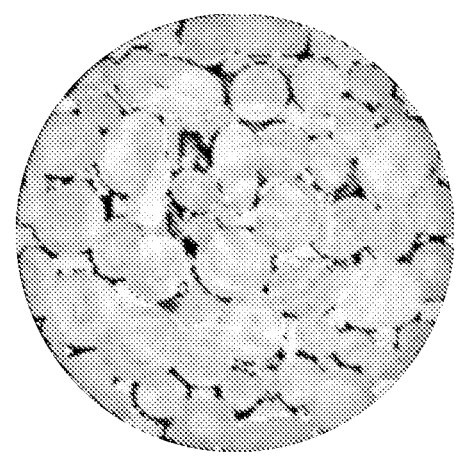
FIG. 6B
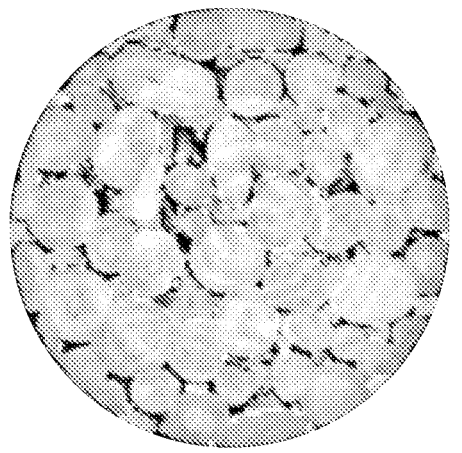
FIG. 6C
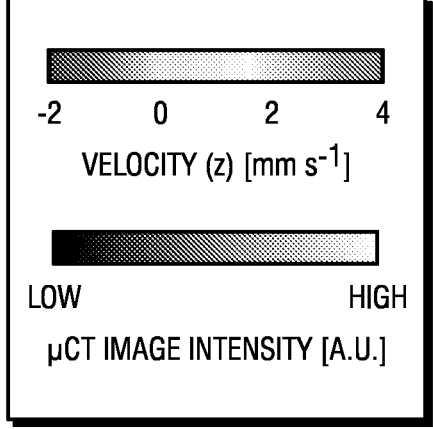

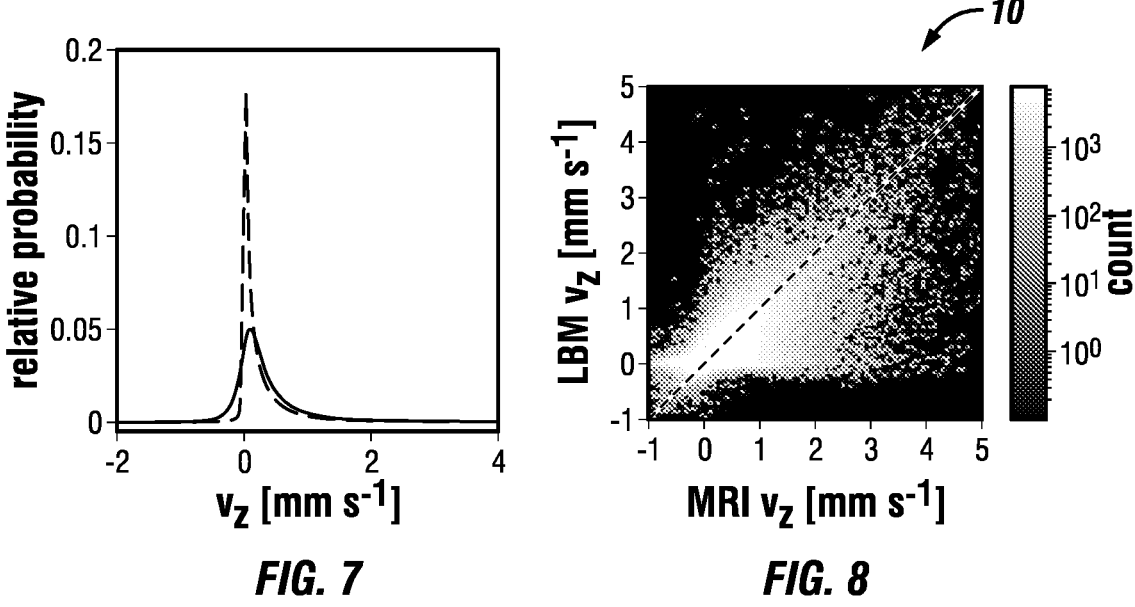
FIG. 7                    FIG. 8
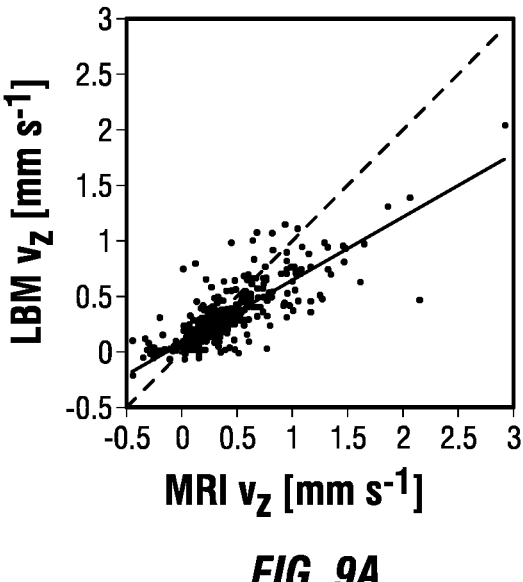
FIG. 9A
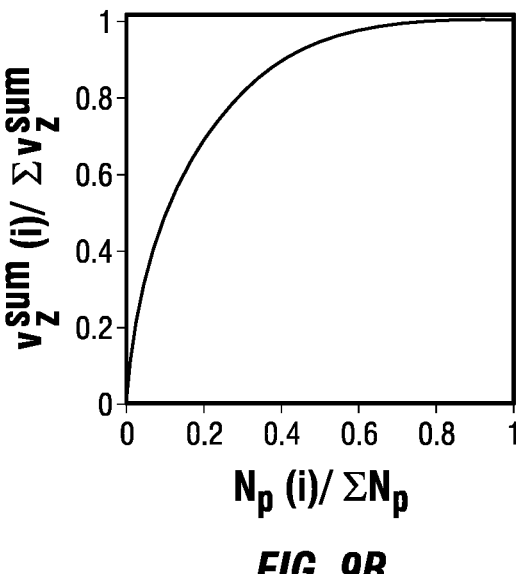
FIG. 9B

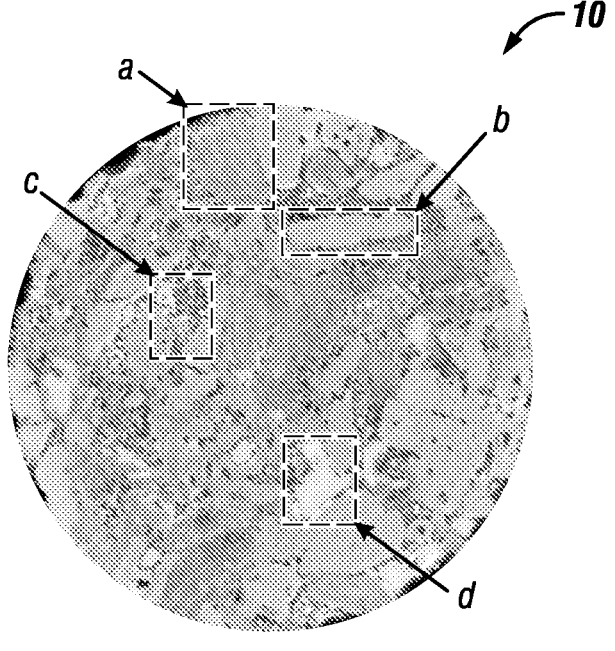
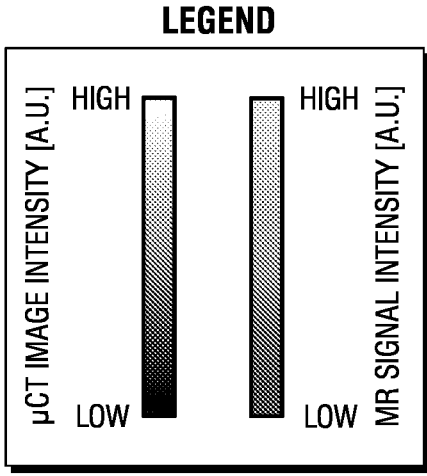
FIG. 10

LEGEND FOR FIGS 11A-11I

-2    0    5    LOW    HIGH

VELOCITY (z) [mm s$^{-1}$]    μCT IMAGE INTENSITY [A.U.]

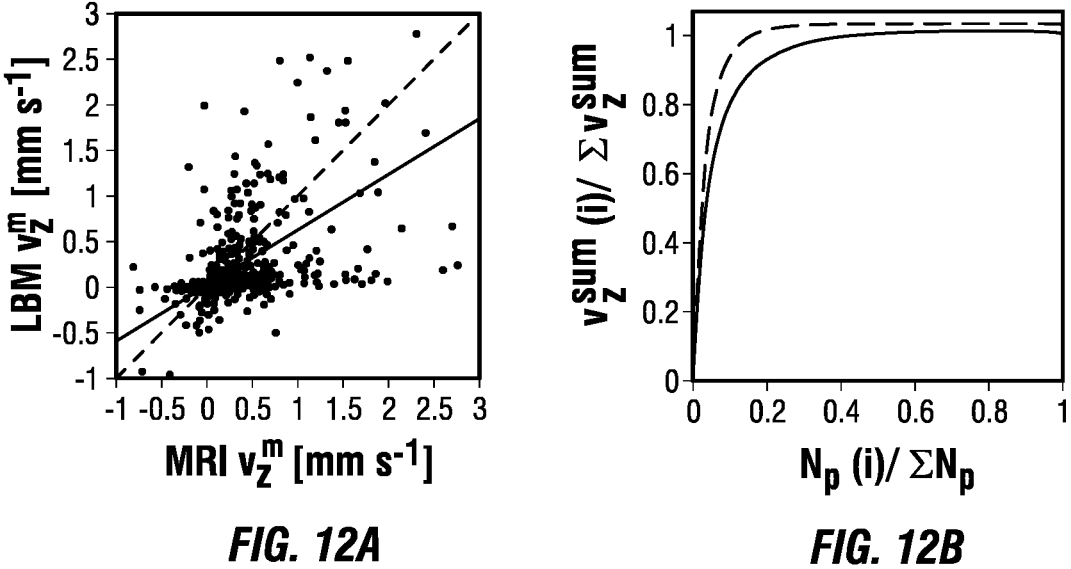
*FIG. 12A*                                        *FIG. 12B*
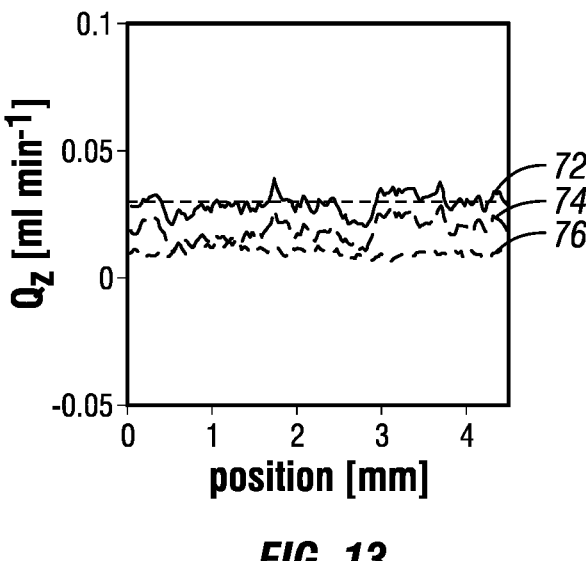
*FIG. 13*

CALIBRATING DIRECT FLOW SIMULATIONS OF ROCK SAMPLES

CROSS REFERENCE TO RELATED APPLICATIONS

This is a National stage application of International Application No. PCT/US2021/057707, filed 2 Nov. 2021, which claims priority of U.S. provisional Application No. 63/109, 074, filed 3 Nov. 2020 and U.S. provisional Application No. 63/111,133, filed on 9 Nov. 2020 which is incorporated herein by reference in its entirety.

FIELD OF THE INVENTION

The present disclosure relates to the field of direct flow simulations of rock samples. In particular, the method calibrates direct flow simulations with 3D images generated by Digital Rock physics enhanced by flow-magnetic resonance imaging (flow-MRI).

BACKGROUND OF THE INVENTION

Analytical and imaging techniques that can help visualise fluid flow in the pore space of sedimentary rocks are of significant interest for the oil and gas industry. In the face of a growing global energy consumption, with a need to reduce pressure on the environment, enhanced oil recovery (EOR) and carbon capture and sequestration (CCS) may be part of a future in which hydrocarbons are produced in a more sustainable manner. Through EOR, more hydrocarbons can be sourced from a single well by injection of brine, polymers, or surfactants, thereby reducing the need for additional drilling. In CCS, carbon dioxide is re-injected into a reservoir so that it does not enter the atmosphere. Fluid flow and dispersion in rock also drives the process of geothermal heat extraction, which is another promising source of renewable energy. Understanding fluid flow properties plays a key role in the fine-tuning and deployment of such technologies.

However, numerous factors influence fluid flow, including, for example, fluid density and viscosity, interfacial tension, fluid flow rate, surface wettability and pore geometry. Laboratory tests for these factors require substantial time and are quite expensive. Further, the number of samples that may be processed is relatively limited due to the time and expense required to conduct each test. There is a need for providing information more quickly in order to make more timely decisions.

Many in the industry are turning to simulations of fluid flow in a reservoir for making informed decisions in a timely manner. Pore-scale flow simulation, based on an understanding of the dynamics of fluid displacement at the pore-scale, can facilitate computation of Darcy-scale flow parameters used as inputs, for example, in reservoir simulation.

Direct flow simulations are widely used to predict fluid flow and transport through complex porous rocks. One type of simulator is based on the lattice-Boltzmann method (LBM), which simulates the collision and streaming of microscopic particles, and then evaluates the macroscopic pressure gradient and velocity, from which the permeability of a porous material can be estimated (Chen et al. "Lattice Boltzmann method for fluid flows" *Annu Rev Fluid Mech* 30:329-64; 1998). For example, Alpak et al. ("Prediction of fluid topology and relative permeability in imbibition in sandstone rock by direct numerical simulation" *Advances in Water Resources* 122:49-59; 2018 and "Direct simulation of pore-scale two-phase visco-capillary flow on large digital rock images using a phase-field lattice Boltzmann method on general-purpose graphics processing units" *Computational Geosciences* 23:849-880; 2019) describe an energy-based LBM (eLBM) that is a two-phase flow simulation system composed of three modules: forced drainage simulation module, forced imbibition simulation module, and a steady-state relative permeability computation module.

Before such simulators can be effectively used as a predictive tool, their output should be validated against experimental data. Earlier studies have compared nuclear magnetic resonance (NMR) and magnetic resonance imaging (MRI) measurements of flow in porous materials (flow-MRI) and direct flow simulations in porous materials. However, while good qualitative agreement was shown between the experimental velocity map and the simulation, LBM simulations tended to overpredict large axial (in the superficial flow direction) velocities, but underpredict low axial velocities.

MRI and flow-MRI are helpful tools for characterising the microstructural and mass transport properties in porous media. Such data are conventionally acquired at spatial resolutions of a few hundred microns that are too coarse for adequately capturing pore-scale information in porous rocks. Accordingly, there is a need to increase the spatial resolution of MRI acquisitions by 1-2 orders of magnitude for exploring structure-transport relationships at spatial resolutions closer to that of the relevant pore scale. However, 3D MRI acquisitions at this spatial resolution is impractical due to prohibitively long acquisition times. Rapid 3D MRI acquisition methods, such as RARE (rapid acquisition with relaxation enhancement), alleviate the problem by significantly reducing the acquisition time.

De Kort et al. ("Under-sampling and compressed sensing of 3D spatially-resolved displacement propagators in porous media using APGSTE-RARE MRI" *Mag Res Imaging* 56: 24-31; 2019) present a schematic of the flow-MRI pulse sequence to acquire spatially-resolved propagators. This sequence combines an alternating pulsed gradient stimulated echo (APGSTE) sequence that is used to encode for displacements, with the RARE imaging sequence used in the velocity imaging sequence.

Karlsons et al. ("Identification of sampling patterns for high-resolution compressed sensing MRI of porous materials: 'Learning' from X-ray micro-computed tomography data" *J. Microsc.* 276: 63-81; 2019) discloses data sampling patterns to achieve undersampling schemes for compressed sensing MRI (CS-MRI) acquisitions.

Digital rock physics is a technology that has been developed to provide faster, more, and less expensive analysis of hydrocarbon-containing formation rocks to determine key petrophysical characteristics of the rocks. Digital rock physics utilizes digital images of formation rocks to simulate rock multiphysics at the pore scale and to predict properties of complex rocks. A major focus of DR technology is to accurately simulate fluid flow behaviour within the pore space in order to predict petrophysical properties, for example permeability, of a sample.

There is a need for a method for calibrating direct flow simulations of a rock sample using flow-MRI images acquired at spatial resolutions that are compatible with pore-scale direct flow simulations.

SUMMARY OF THE INVENTION

According to one aspect of the present invention, there is provided a method for calibrating a direct flow simulation of a rock sample, the method comprising the steps of: providing a 3D image of a rock sample, wherein the 3D image is comprised of a plurality of voxels; generating a segmented structural image of the rock sample from the 3D image by selecting each of the plurality of voxels to represent either a pore space or a solid material; simulating fluid flow on the segmented structural image with a direct flow simulation; generating a 3D spatially-resolved fluid velocity map for one or more fluid phases at a pore-scale resolution using pulsed field gradient nuclear magnetic resonance imaging; and comparing the simulated fluid flow and the 3D spatially-resolved fluid velocity map; thereby calibrating the direct flow simulation across the rock sample.

BRIEF DESCRIPTION OF THE DRAWINGS

Several of the drawings illustrating non-limiting examples of the present invention are executed in colour as originally filed and not readily converted to black and white in a manner that illustrates the information being conveyed. The colour drawings will also be submitted for publication in a non-patent venue.

The method of the present invention will be better understood by referring to the following detailed description of preferred embodiments and the drawings referenced therein, in which:

FIGS. 6A-6C provide a colour-coded visual comparison of a direct flow simulation and the co-registered image for the Ketton rock sample in the non-limiting example of the present invention, with a grey-scale for μCT image intensity (ranging from black at low intensity to white at high intensity) and a colour-coded scale for velocity (ranging from blue at −2 mm/s to red at 4 mm/s);

FIG. 7 is a graphical depiction of velocity distributions for the direct flow simulation and MRI velocity map for the Ketton rock sample in the non-limiting example of the present invention;

FIG. 8 is a 2D histogram showing voxel-by-voxel correlation between the direct flow simulation and MRI velocity map for the Ketton rock sample in the non-limiting example of the present invention;

FIGS. 9A and 9B are graphical pore-scale comparisons for the direct flow simulation and MRI velocity map for the Ketton rock sample in the non-limiting example of the present invention;

FIG. 10 is a colour-coded 2D slice image from a 3D co-registered image for the Estaillades rock sample in the non-limiting example of the present invention, with a grey-scale for μCT image intensity (ranging from black at low intensity to white at high intensity) and a colour-coded scale for MR signal intensity (ranging from blue at low intensity to green at high intensity);

FIGS. 11A-11I provide a colour-coded visual comparison of a LBM simulation and the MRI velocity map for the Estaillades rock sample in the non-limiting example of the present invention, with a grey-scale for μCT image intensity (ranging from black at low intensity to white at high intensity) and a colour-coded scale for velocity (ranging from blue at −2 mm/s to red at 5 mm/s;

FIGS. 12A and 12B are graphical pore-scale comparisons for the direct flow simulation and MRI velocity map for the Estaillades rock sample in the non-limiting example of the present invention; and FIG. 13 is a graphical comparison of flow rates for each image slice in the middle region of the Estaillades rock sample in the non-limiting example of the present invention.

DETAILED DESCRIPTION OF THE INVENTION

The present invention provides a method for quantitatively visualizing fluid transport properties of a rock. In accordance with the present invention, a direct flow simulation of fluid flow is compared with 3D spatially-resolved fluid velocity maps to calibrate the direct flow simulation across the rock sample. By better understanding the flow and distribution of the fluid across the rock sample, better decisions can be made with respect to recovery of hydrocarbons from a subterranean formation, carbon capture and sequestration in the subterranean formation, and/or a geothermal heat extraction process.

Flow-MRI provides the ability to quantitatively and non-invasively measure 3D spatially-resolved fluid flow fields in rock samples. By looking at the spatially-resolved flow fields, it is possible to identify whether the microscopic flow phenomena that lie at the basis of the prediction of core-scale petrophysical properties are correctly simulated. Furthermore, spatially-resolving flow properties provide fundamental insight into the degree of spatial heterogeneity of the flow across the rock sample.

Figure 1:
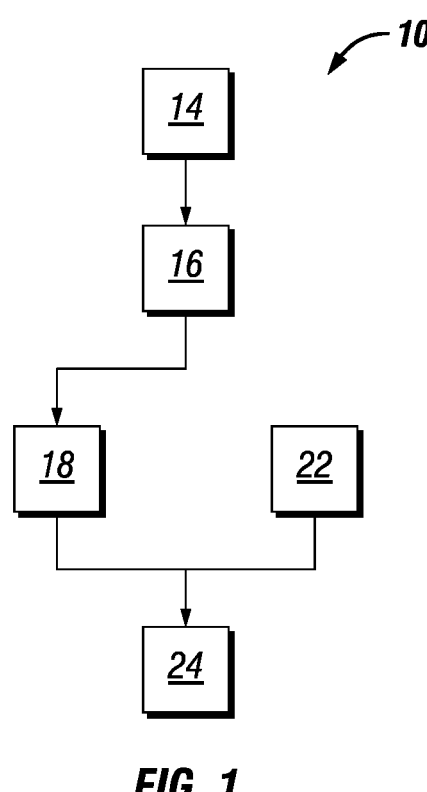
FIG. 1 is a block flow diagram illustrating steps of one embodiment of the present invention.

Referring now to FIG. 1, one embodiment of the method of the present invention 10 involves providing a 3D image of the rock sample at step 14 and generating a segmented structural image of the rock sample at step 16. The segmented structural image identifies pore spaces and solid material in each voxel of the segmented structural image. At step 18, fluid flow is simulated on the segmented structural image with a direct flow simulation.

Petrophysical properties of rock samples have been measured using Digital Rock technology using segmented structural images. Although these macroscopic, or bulk, properties are critical to any petrophysical analysis, they provide limited insight into the degree of spatial variation of these properties. Heterogeneity in petrophysical properties is a key factor underlying the efficiency of hydrocarbon recovery processes. The present inventors have surprisingly discovered that Digital Rock technology is enhanced by spatially-resolving fluid flow in rock samples. Therefore, in accordance with the present invention, a 3D spatially-resolved fluid velocity map is generated for one or more fluid phases at step 22.

The simulated fluid flow and the velocity map are compared in step 24 to correlate the pore structure of the rock sample with fluid flow in the pores. By comparing the pore structure to the direct simulation of fluid flow and the 3D spatially-resolved velocity map, the direct flow simulation can be calibrated. The comparing step may be conducted by visual comparison between pore structure images and fluid flow simulation images and the 3D spatially-resolved velocity map. In a preferred embodiment, the comparison includes co-registering the simulated fluid flow and the 3D spatially-resolved fluid velocity map to produce a co-registered 3D image. The co-registered 3D image is used for calibrating the direct flow simulation at all positions within the rock sample.

Figure 2:
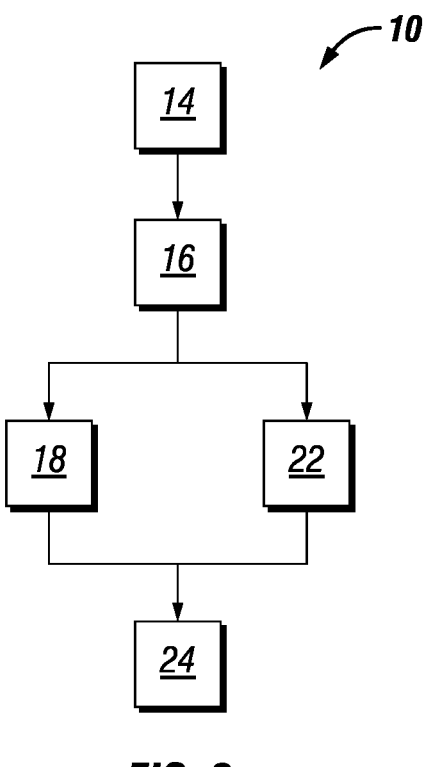
FIG. 2 is a block flow diagram illustrating steps of another embodiment of the present invention.

In the embodiment of FIG. 2, the segmented structural image generated in step 18 is used for generating the 3D spatially-resolved fluid velocity map at step 22. In this embodiment, the segmented structural image is used to optimize the data under-sampling pattern for the experiment. The under-sampled data acquired according to that pattern is then reconstructed using compressed sensing.

3D Images

A 3D image of a rock is obtained from a rock from a formation for which the fluid transport properties are of interest. As an example, the rock may be a sandstone, a carbonate, a shale and combinations thereof from a hydrocarbon-containing formation. Alternatively, the rock may be from a subsurface formation for which carbon sequestration is being considered. The rock may be obtained by conventional means for obtaining rock samples from a formation. In a preferred embodiment, a core sample of the rock is obtained by coring a portion of the formation from within a well in the formation, for example, a whole core or a sidewall core. Alternatively, a sample of the rock may be obtained from drill cuttings, preferably undisturbed drill cuttings, produced in drilling a borehole in the formation. The rock may be obtained from the same borehole as the electrical property measurement. Alternatively, the rock may be obtained from another borehole in the same field as the borehole for which the electrical property measurement was produced.

The rock sample should be of sufficient size to obtain a 3D image of sufficient volume at the scale that the image is generated. In particular, the rock sample should be of sufficient size such that characteristics of the bulk of the sample predominate over the characteristics of the edges of the sample at the scale or field of view of the image to be generated.

A 3D image comprised of a plurality of voxels is obtained from the rock sample. The 3D image of the rock may be obtained utilizing pore-scale imaging technology. A 3D image of the rock may be obtained by, for example, without limitation, by scanning electron microscopy (SEM), X-ray computed tomography, acoustic microscopy, magnetic resonance imaging, and the like. X-ray computed tomography includes, without limitation, X-ray micro-computed tomography (micro-CT) and X-ray nano-computed tomography (nano-CT). Most preferably, the 3D image of the rock is obtained by micro-CT to provide sufficient field of view of the rock to avoid edge pores distorting the overall porosity of the resulting image, as well as to reduce scanning time and computational requirements that higher resolution tomography (e.g. nano-CT) would require.

The 3D image of the rock obtained by pore-scale imaging technology is comprised of a plurality of voxels, where the volume defined by each voxel represents a maximum resolution of the image. The resolution of the image should be selected to provide a voxel size at which the dominant pore throats for fluid flow in the rock are sufficiently resolved and at which a sufficient field of view is provided so as to be representative of the whole rock for a fluid transport property to be analysed.

The resolution of a micro-CT image may be chosen based on the size of the rock sample, the relative average pore size of the type of rock, the time required for the imaging, and the computational power required to store and conduct further computational activity on the image data. The pore-scale resolution of the micro-CT image may range from 0.1 $\mu m^3$ to 30 $\mu m^3$ per voxel. For sandstones, the micro-CT image is preferably produced at a resolution in a range from 1 $\mu m^3$ to 25 $\mu m^3$ per voxel, more preferably from 2.5 $\mu m^3$ to 15 $\mu m^3$ per voxel. For carbonates, the resolution of the micro-CT image is preferably produced at a resolution in a range from 0.5 $\mu m^3$ to 20 $\mu m^3$ per voxel, more preferably from 1 $\mu m^3$ to 10 $\mu m^3$ per voxel. For shales, the resolution of the micro-CT (or nano-CT) image is preferably produced at a resolution in a range from 0.1 $\mu m^3$ to 10 $\mu m^3$ per voxel, more preferably from 0.5 $\mu m^3$ to 5 $\mu m^3$ per voxel.

In a preferred embodiment, the acquired image may be processed to reduce noise and image artefacts. Noise may be filtered from the acquired image by filtering using a local means filter to reduce noise. Imaging artefacts, predominant at the outer edges of the acquired image, may be reduced by processing the image while excluding the outer edges of the image.

Segmenting

The 3D image obtained for the rock is processed to segment the voxels of the image into voxels representing either pore space in the rock or solid material in the rock, thereby producing a binary image in which pore voxels have a value of zero and solid material voxels have a value of one (or vice versa). The image may be a grayscale image, and processing the voxels of the image to segment the image into voxels representing pore space or solid material may be effected by assigning a voxel a designation as pore space or as solid material based on a threshold, wherein voxels having an image intensity above the threshold may be assigned a value representing a pore (or solid material) and voxels having an image intensity below the threshold may be assigned a value representing solid material (or a pore). A threshold may be calculated using Otsu's method as described in Otsu ("A Threshold Selection Method from Gray-level Histogram" *IEEE Trans. SMC* 9:62-66; 1979), or other threshold calculation algorithms known in the art.

Segmentation algorithms are known to those skilled in the art. Preferably, the segmentation method is selected to identify pore space from solid matrix. Examples of segmentation methods are described in Otsu ("A Threshold Selection Method from Gray-level Histogram" *IEEE Trans. SMC* 9:62-66; 1979), Andra et al. ("Digital Rock Physics Benchmarks-Part II: Computing Effective Properties" *Computers and Geosciences* 50:33-43; 2013), Saxena et al. ("Effect of Image Segmentation & Voxel Size on Micro-CT Computed Effective Transport & Elastic Properties" *Marine and Petroleum Geology* 86:972-990; 2019), and Chuang et al. ("Fuzzy C-Means Clustering with Spatial Information for Image Segmentation" *Comput. Med. Imaging Graph.* 30:9-15; 2006). The desired selection of segmentation will be understood by those skilled in the art. Segmentation using segmentation algorithms is preferably conducted automatically using data processing systems.

In a preferred embodiment, the 3D image is segmented by the watershed-based segmentation algorithm (Beucher et al. "The morphological approach to segmentation: The watershed transformation" in: E. R. Dougherty (Ed.), Math. Morphol. Image Process, Marcel Dekker Inc., New York, 1993: pp. 433-481).

Direct Flow Simulation

In accordance with the present invention, fluid flow is simulated on the segmented structural image with a direct flow simulation. Direct flow simulations include, for example, without limitation, finite difference methods, finite element methods, finite volume methods, and lattice Boltzmann methods. In a preferred embodiment, fluid flow is simulated with an LBM simulator. Examples of LBM simulators include, without limitation, an energy-based LBM (eLBM) simulator and a multiple-relaxation-time (MRT) LBM simulator.

Spatially-Resolved Fluid Velocity Mapping

The fluid velocity map is obtained experimentally. In accordance with one embodiment of the present invention, the segmented structural image is also used to generate a 3D spatially-resolved fluid velocity map for one or more fluid phases at a pore-scale resolution using pulsed field gradient nuclear magnetic resonance imaging.

Preferably, the 3D spatially-resolved fluid velocity map is generated by using compressed sensing (CS) to reconstruct spatially-resolved fluid-flow encoded phase-difference maps for each of the fluid phases under flowing conditions, and calculating a flow velocity map for each of the fluid phases. The flow velocity map is preferably calculated by applying a correction for any spurious phase angle shifts introduced by the rapid acquisition with relaxation enhancement (RARE) MRI pulse sequence. Preferably, the correction is applied by subtracting the stationary phase difference from the phase difference measured under flowing conditions.

MRI has been widely used to study porous materials, including porous rock core plugs, because it provides a direct and non-invasive way to obtain quantitative chemical, microstructural, and transport-related information within optically opaque materials saturated with fluid. Due to the relatively low sensitivity of the magnetic resonance (MR) method, such MRI data are typically acquired at spatial resolutions on the order of a few hundred microns. However, the pore sizes in sedimentary rocks are typically smaller than 100 µm. There is a need to increase the spatial resolution of MRI measurements to be able to obtain local structure-transport correlations at spatial resolutions similar to that of the relevant pore scale.

CS in MRI is based on the following requirements, for example, (1) aliasing artefacts (e.g., the sample data) in the linear reconstruction must be incoherent and noise-like; (2) the desired image exhibits transform sparsity; and (3) the image is reconstructed using a non-linear algorithm that enforces sparsity and consistency with the acquired k-space data.

As discussed in Karlsons et al. (2019), it is possible to acquire 3D MRI images, using a combination of rapid and under-sampled MRI data acquisitions and CS, at a spatial resolution of 17.6 µm (carbonate rock), which is at least an order of magnitude higher than the resolution of conventional MRI, and is a resolution at which pore-scale features in many rocks can be clearly discerned. CS significantly reduces the experimental acquisition time by using prior knowledge to reconstruct images on the basis of an under-sampled data space.

In CS flow MRI (Benning et al. "Phase reconstruction from velocity-encoded MRI measurements—A survey of sparsity-promoting variational approaches" *J Magnetic Resonance*, 234:26-43; 2014; Lustig et al. "Sparse MRI: The application of compressed sensing for rapid MR imaging" *Magnetic Resonance in Medicine* 58:1182-1195; 2007), the goal is to recover the phase of a complex-valued image, m, from an acquired under-sampled k-space dataset, y. CS enables a solution for m, $m_{CS}$, using a variational regularisation approach that incorporates prior knowledge about m into the reconstruction process. In the case of the CS reconstruction, the prior knowledge is that the image can be sparsely represented in an appropriate transform domain.

The type of regularisation functional J that is used to map the image into the transform domain depends on the nature of the image to be mapped. For instance, a non-smooth regularizer, such as Total Variation (TV), may be more suited to an image with sharp-edges whereas a smooth regularizer, such as the Daubechies wavelet transform, lends itself well to images in which the pixel intensities change more gently.

In one embodiment, TV regularisation, based on the finite-difference transform of m, is used for CS reconstruction. Using a non-linear recovery algorithm, a solution for $m_{CS}$ is computed on the basis of this prior knowledge, expressed as $$m_{CS} \in \arg\min_{m} \left\{ \frac{1}{2} \|y - \mathcal{F}_u m\|_2^2 + \alpha J(m) \right\}, \tag{1}$$

where $\alpha$ is a regularisation parameter that balances the weight between the fidelity term $$\frac{1}{2} \|y - \mathcal{F}_u m\|_2^2$$

and the regularisation term $\alpha J(m)$. The value of the parameter $\alpha$ was chosen on the basis of Morozov's discrepancy principle, which is written as $$\|y - \mathcal{F}_u m\|_2 \leq \sigma_n \sqrt{n}, \tag{2}$$

where n is the number of k-space samples. The maximum value of $\alpha$ which satisfies the condition in Equation (2) was chosen for the reconstructions.

The imaging may be performed to selectively measure various fluids, such as hydrocarbons (e.g. crude oil or dodecane) and aqueous fluids (e.g., water, brine, etc.), in the core sample. Such techniques may be used to image the various fluids in the formation separately or in combination. In particular, the imaging may be used to differentiate between aqueous fluids and hydrocarbons in the core samples. These images may be used, for example, to characterize fluid parameters, such as rate of flow and type of hydrocarbons produced. Information gathered from such imaging may be used, for example, to identify specific fluids, individually image fluids, evaluate the formation containing the fluid, determine downhole parameters, detect valuable hydrocarbons, provide information for planning oilfield operations, among others. The flow imaging is conducted while pumping one or more fluids, alone or in combination, through the rock sample. A stationary condition is imaged by discontinuing the fluid pumping.

Flow-MRI is an integration of a pulsed field gradient nuclear magnetic resonance (PFG NMR), which is used to quantify fluid displacements, with MRI, which spatially-resolves those displacements. Preferably, the PFG NMR is combined with a RARE MRI pulse sequence.

Figure 3A:
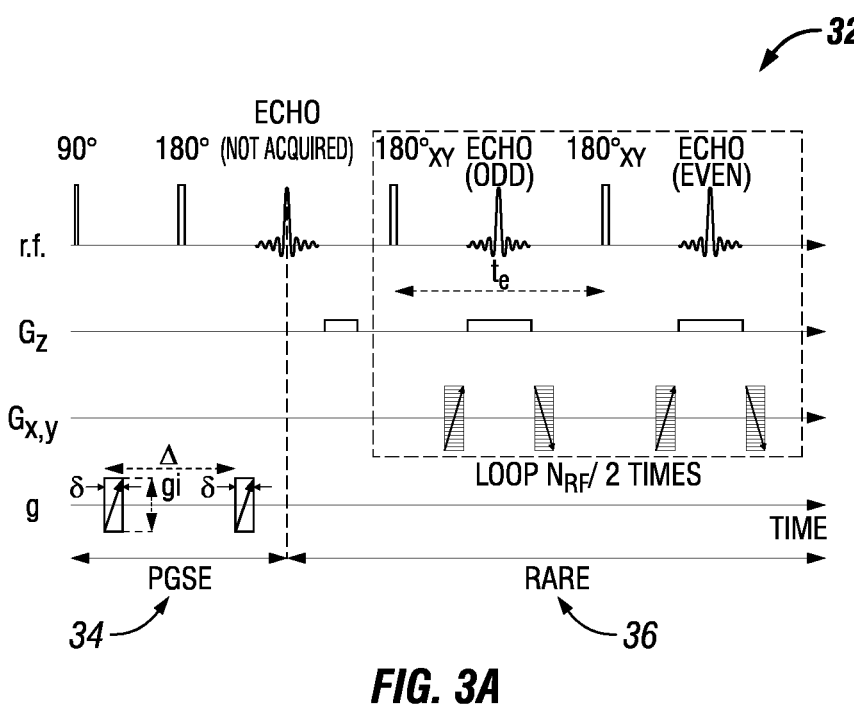
FIG. 3A is a schematic of an example PGSE-RARE flow-MRI pulse sequence that may be used to acquire a velocity map in one embodiment of the present invention.

A schematic of a velocity-encoded flow-MRI pulse sequence used to acquire velocity maps is shown in FIG. 3A, which will be discussed in more detail in the Examples. The pulse sequence combines a PGSE sequence that is used to encode for velocities, with a RARE imaging sequence that is used to spatially-encode the measured velocities. The RARE imaging sequence is well-suited for CS applications and imaging fluid-saturated porous rocks. A PGSE sequence for velocity encoding is preferred because the observation time is short compared to signal decay rates in the transverse plane. Accordingly, signal loss is small compared to using a stimulated echo sequence, which would inherently suffer from a 50% loss of signal. In one preferred embodiment of the present invention, both the RARE imaging sequence and a CS approach are exploited to speed up acquisition and to enable 3D velocity maps at 35 μm spatial resolution.

In another embodiment of the present invention, a spatially-resolved displacement propagator is acquired. Displacement propagators are probability distributions of molecular displacements, $\overline{P}(R, \Delta)$, where $\overline{P}$ is the probability that a spin moves over a dynamic displacement, $R=r'-r$, in an observation time, $\Delta$ (typically in the range between a few ms up to the spin-lattice relaxation time, $T_1$, of the fluid which may be up to a few seconds). By spatially-resolving the propagator, information about local, time-dependent flow dispersion, which arises due to molecular self-diffusion of fluid molecules across streamlines, can be obtained, as well as measurements of flow velocity.

Figure 3B:
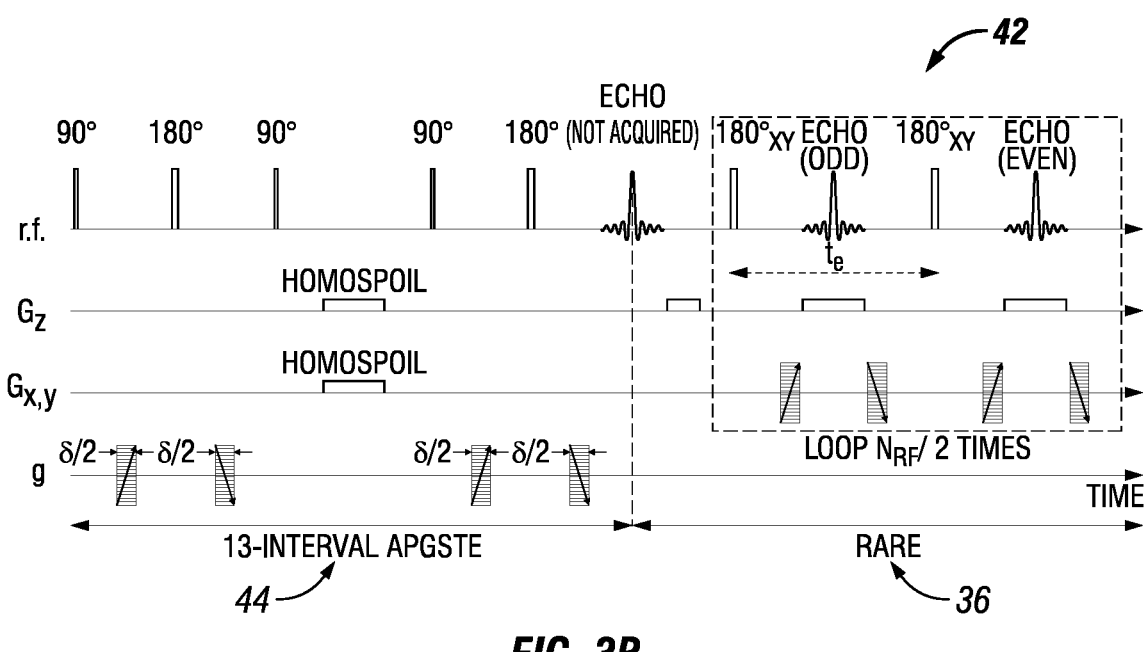
FIG. 3B is a schematic of an example APGSTE-RARE flow-MRI pulse sequence that may be used to acquire spatially-resolved propagators in another embodiment of the present invention.

A schematic of the pulse sequence to acquire spatially-resolved propagators is shown in FIG. 3B, which will be discussed in more detail in the Examples. This sequence combines an alternating pulsed gradient stimulated echo (APGSTE) sequence that is used to encode for displacements, with the RARE imaging sequence used in the velocity imaging sequence. A stimulated echo sequence provides longer observation times for propagator measurements. The APGSTE, or Cotts 13-interval (Cotts et al. "Pulsed field gradient stimulated echo methods for improved NMR diffusion measurements in heterogeneous systems" *J Magnetic Resonance* 83:252-266; 1999), sequence, which is based on a stimulated echo sequence, utilises alternated pulsed gradients to reduce signal loss due to motion in background field gradients and is well suited to measurement of flow in porous media. Alternatively, a pulsed gradient simulated echo (PGSE) sequence may be used to encode for displacements.

In one embodiment of the present invention, a single, average velocity is spatially-resolved for each of the voxels within an image—a method referred to as velocity mapping. One method that can be used to acquire velocity mapping is a pulsed gradient spin echo (PGSE) sequence. Preferably, the PGSE is used with a RARE imaging sequence.

Under-sampled k-space datasets under flow and stationary conditions are reconstructed separately to yield complex-valued MRI images. Velocity maps are then calculated from these phase maps as described above. Preferably, background noise is reduced, more preferably nulled, by generating a binary mask from the stationary MRI datasets and multiplying the flow phase maps with the binary mask.

A 3D velocity map is generated from the flow phase and preferably, stationary velocity maps to show the main flow channels through a rock sample. The 3D velocity map provides a visualization of the heterogeneity of a rock sample and the presence of higher velocity flow channels. Further, regions of the rock that have low fluid mobility and/or stagnant fluid can be visualized. Finally, negative velocities illustrate the occurrence of backflow through a porous rock and is believed to be caused by re-circulating flow patterns in immediate vicinity of surfaces, or vortex-like structures at the meeting points of streamlines.

According to the method of the present invention, high-resolution MRI velocity maps that are capable of non-invasively capturing flow information in pore space are compared with direct flow simulations, run on segmented 3D μCT images rock core plugs.

In a preferred embodiment of the method of the present invention, the results of the flow simulation are compared to the MRI flow map by co-registration and coarse-graining of the simulation down to the same resolution as the flow MRI data. Co-registering the simulated fluid flow with the 3D velocity map allows the simulated fluid flow to be calibrated with experimentally generated velocity maps. This is particularly advantageous for rock having structural heterogeneity and/or fluid flow in pores below resolution of the 3D image.

X-ray μCT images of small rock plugs are acquired at resolutions of a few microns, i.e., an order of magnitude higher than the currently accessible resolution with flow MRI. But, in particular for heterogeneous carbonate rocks, the smallest (micro)pores are still significantly smaller than the voxel size currently accessible with X-ray μCT. The areas in the rock where microporosity is present, will have a lower average X-ray absorption because of the globally lower mass density of that area—but such a microporous area cannot be distinguished from a non-porous area with a lower mineral density such that the X-ray absorption is effectively identical, unless the rock is saturated with a doped fluid.

A challenge of conventional methods is in understanding the extent to which these smaller pores actually contribute to the overall flow of fluid through the rock, and therefore to what extent a simulation of the flow field based on a μCT-derived pore space is accurate. Although in many cases, the microporosity of the rock is not expected to carry significant flow, some regions of the microporous carbonate rocks can be connected only by microporosity in which case the contribution to flow by micropores can become significant.

In accordance with the present invention, comparison of 3D velocity maps with the simulated fluid flow makes it possible to non-invasively differentiate between these two. MRI is sensitive only to fluids and will therefore reveal only the fluid-saturated micropores, but not the areas of solid rock in which no fluid is located. In the embodiment of the present invention where the comparison step includes co-registering the 3D velocity map with the simulated fluid flow, the co-registered 3D image provides an average fluid flow velocity for each voxel in the segmented structural image.

The images depicting fluid flow through the rock are co-registered in a predetermined flow direction to determine distribution of fluid flow across the rock sample. Image co-registration can be accomplished with a software tool including, for example, without limitation, by the "Register Images" module in AVIZO™ 2019.4 (FEI Visualization Sciences Group, USA).

In one embodiment of the present invention, the segmented structural image is co-registered with the spatially-resolved fluid velocity map. In another embodiment of the present invention, the alignment of the co-registered structural and velocity map is optimized using rigid transformations. The transformed image is then co-registered with the direct flow simulation.

In yet another embodiment of the present invention, the co-registered image is resampled onto the MRI data coordinate system using a Lanczos filter (Duchon, "Lanczos Filtering in One and Two Dimensions" *J. Appl. Meteorol.* 18: 1016-1022; 1979), which enables MRI flow maps and 3D images, including LBM simulations, to be visualised and compared on the same grid.

EXAMPLES

The following non-limiting examples of embodiments of the method of the present invention as claimed herein are provided for illustrative purposes only.

The rock samples used in this example were a Ketton limestone rock core plug (3.84±0.01 mm in diameter and 11.10±0.37 mm in length) and an Estaillades limestone core plug (3.92±0.02 mm in diameter and 12.65±0.13 mm in length). The samples were dried in an oven at 70° C. for 12 h.

Example 1—Structural Imaging

The dried Ketton sample was imaged using a Bruker SKYSCAN 1172™ micro-CT scanner (Bruker Micro-CT, Belgium) at an isotropic resolution of 5.00 μm. Image acquisition was performed using a source voltage 60 kV, a source current of 165 μA, and an Al (0.5 mm) filter. 802 projection images were acquired by rotating the sample in angular increments of 0.25° over 200.5° with 10 scans per angular increment, yielding a total acquisition time of 11.4 h. Projection images were reconstructed using the NRE-CON™ software (Bruker, v1.6.8.0) to give 2666 cross-sectional slices.

The dried Estaillades sample was imaged using a Bruker SKYSCAN 2214™ micro-CT scanner (Bruker Micro-CT, Belgium) at an isotropic resolution of 3.00 μm. Image acquisition was performed using a source voltage 90 kV, a source current of 70 μA, and an Al (1 mm) filter. To image the entire sample, acquisitions were performed at 5 different scanning positions along the longest dimension of the sample. For each position, 3601 projections were acquired by rotating the sample in angular increments of 0.1° over 360° with 6 scans per angular increment, yielding an acquisition time of 4.26 h. Thus, the total acquisition time was 21.3 h. Projection images from all 5 scanning positions were stitched together and reconstructed using the NRECON™ software (Bruker, v1.6.8.0) to give 4319 cross-sectional slices.

Figure 4A:
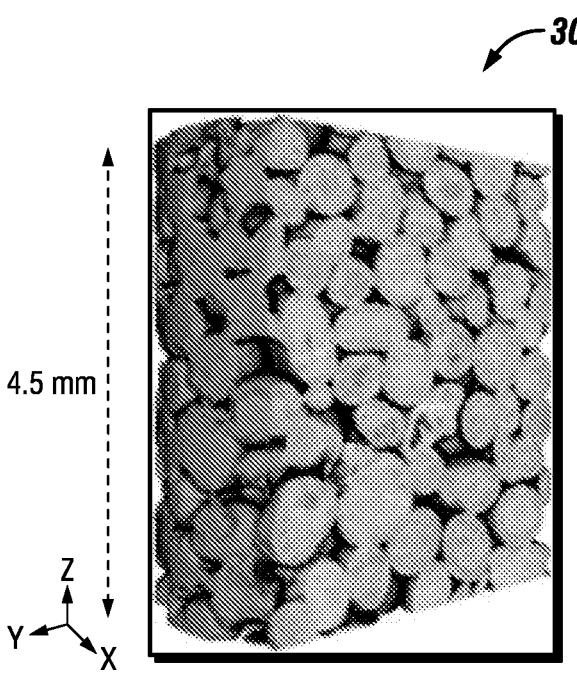
FIGS. 4A and 4B are 3D sections extracted from micro-CT images of Ketton and Estaillades rock samples prepared in a non-limiting example to the present invention.
Figure 4B:
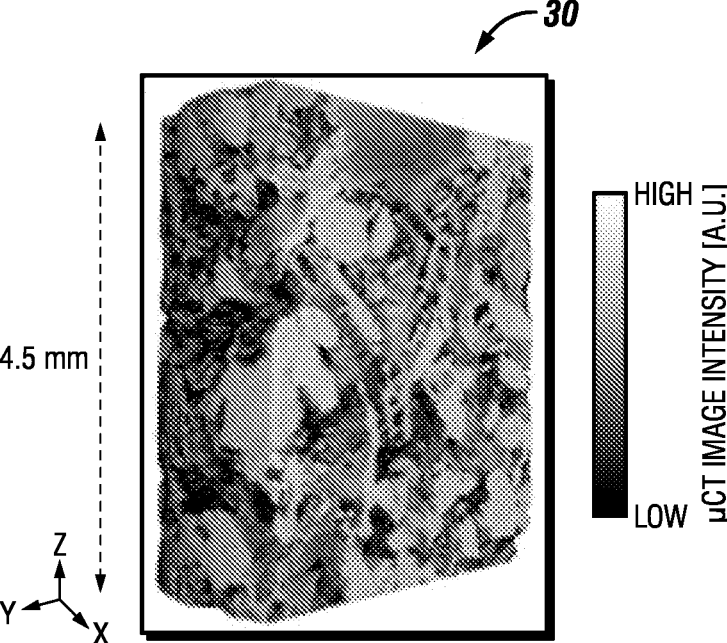

3D μCT images of the rock samples were generated by successively stacking all 2D cross-sectional slices. 3D sections 20 extracted from the μCT image of the rock samples, are shown in FIGS. 4A and 4B, for the Ketton and Estaillades rock samples, respectively.

The 3D μCT images were then segmented using the watershed-based segmentation algorithm (Beucher et al., 1993) in AVIZO™ 2019.4 (FEI Visualization Sciences Group, USA). Binarized structural images were generated by assigning all non-zero phases to the 1 phase which is intended to represent impermeable solids. The pore spaces of the binarized structural image were separated into individual pores using a Chamfer distance transform and marker-based watershed algorithm.

The rock samples were vacuum-saturated with deionised water. Pore network properties were extracted from the μCT images of Ketton and Estaillades rock core plugs, as shown in Table 1. The properties were extracted from the connected pore-space images. The spatial resolution of the images was 7 μm for the Ketton sample and 3 μm for the Estaillades sample.

TABLE 1

| Rock | Porosity $\varphi_g$ (%) | Connected $\varphi_{\mu CT}$ (%) | Average pore radius (μm) | Average throat radius (μm) | Average coordination number |
|---|---|---|---|---|---|
| Ketton | 21 ± 4 | 14 | 111 | 41 | 4.7 |
| Estaillades | 25 ± 1 | 6 | 35 | 15 | 3.6 |

Example 2—Fluid Flow Imaging

For the flow MRI experiments, the samples were placed in Adtech fluorinated ethylene propylene (FEP) heat shrink tubing to connect the sample to inlet and outlet FEP flow line, and to provide confinement for creating a superficial flow direction (z) representing net overall flow. While fluid can also flow in the x and y plane, the net overall flow in the x and y directions will be 0, because the fluid cannot flow out of the sides due to the confinement. In the case of the Estaillades sample, before placing the sample in the heat shrink tubing, two layers of Teflon tape with thickness of 75 μm were applied around the plug to minimise fluid by-passing through vugs and cracks on the surface of the rock during flow experiments. A constant flowrate of water was imposed using a Vindum VP-6™ metering pump.

Three pore scale MRI data sets were acquired: a velocity map and two spatially resolved propagators, with different observation times (Δ), as detailed below. The experiments were carried out on a 7.0 T vertical-bore magnet controlled by a Bruker BIOSPIN AVANCE III HD™ spectrometer. A Bruker MICRO5™ tri-axial gradient system with a maximum gradient strength of 2.9 T m$^{-1}$ in the three orthogonal x-, y-, and z-directions was used to achieve spatial resolution. An 8 mm radio frequency (r.f.) saddle coil tuned to a resonance frequency of 299.84 MHz ($^{1}$H) was used for spin excitation and signal detection.

Example 2A—MRI Data Set 1: Velocity Map

A PGSE-RARE experiment 32, illustrated schematically in FIG. 3A, was used to acquire under-sampled velocity maps. The PGSE-RARE experiment 32 combines a PGSE sequence 34 with RARE imaging sequence 36 for velocity and spatial encoding, respectively. The PGSE 34 velocity encoding is achieved by a pair of unipolar gradients of strength g and duration δ, separated by an observation time, Δ. The RARE 36 spatial encoding is achieved using the frequency-encoding gradient, $G_z$, and the phase-encoding gradients, $G_x$ and $G_y$. A RARE factor ($N_{RF}$) is the number of 180° refocusing pulses in an echo train. $t_e$ is the echo spacing.

Sampling patterns for the acquisition of velocity maps were generated using the μCT-based variable density sampling (μCT-VDS) strategy described in Karlsons et al. (2019). In this example, for the Ketton sample, the method was used to generate optimized k-space sampling patterns with a k-space sampling fraction of 0.25. The duration of the hard excitation and 180° refocusing r.f. pulses were 6.0 μs and 12.0 μs, respectively. A RARE factor ($N_{RF}$) of $N_{RF}$=8 with an echo spacing ($t_e$) of $t_e$=2.2 ms was used to acquire $N_{RF}$ successive lines of k-space for each excitation pulse. To achieve velocity encoding, a pair of unipolar gradients g of amplitude g=2.0 T m$^{-1}$ ($g_i$=4.0 T m$^{-1}$) and duration of δ=ms were used, separated by an observation time Δ=4 ms. With 32 scans for signal averaging and a recycle delay ($t_{RD}$) of $t_{RD}$=1.1 s, the acquisition time of the velocity map was 20 h. Velocities were encoded along the z-direction, i.e., along the superficial flow direction. Images under stationary conditions were also acquired to correct for the velocity offsets. Thus, the total acquisition time of the velocity image with velocities encoded in the superficial flow direction was 40 h. The images were acquired with a field of view (FOV) of 13.5 mm×4.5 mm×4.5 mm and 384 voxels×128 voxels×128 voxels in the frequency-(z) and phase-encoding (x, y) directions, respectively, yielding a 3D velocity map with an isotropic resolution of 35.2 μm.

For the Estaillades sample, under-sampled velocity maps were acquired using the same PGSE-RARE pulse sequence. Under-sampling schemes were generated using the μCT-based variable-density sampling with a k-space sampling fraction of 0.3125. Hard 90° excitation and 180° refocusing r.f. pulses were used with durations of 6.6 μs and 13.2 μs, respectively. The number of echoes in the RARE echo train was $N_{RF}$=8 with an echo spacing $t_e$=2.2 ms. The velocity imaging parameters were $g_i$=2.3 T m$^{-1}$, δ=0.132 ms, and Δ=4 ms. 32 scans were acquired for signal averaging with $t_{RD}$=1.375 s, giving an acquisition time of 31.3 h. The total acquisition time of the offset-corrected velocity map was ~63 h. The velocity maps were acquired with a FOV of 13.5 mm×4.5 mm×4.5 mm and 384 voxels×128 voxels×128 voxels in the z-, x-, and y-directions, yielding a 3D velocity map with an isotropic resolution of 35.2 lam.

Example 2B—MRI Data Sets 2 and 3: Propagators

An APGSTE-RARE experiment 42, illustrated schematically in FIG. 3B, was used for the acquisition of the spatially-resolved propagators. The APGSTE-RARE experiment 42 consists of a 13-interval APGSTE sequence 44 and the RARE imaging sequence 36. The displacement encoding was achieved by gradients g which can be applied in any of the three orthogonal directions (z, x, or y). The displacement-encoding gradient was applied parallel to the superficial flow direction (z). The spatial encoding was achieved by the frequency-encoding gradient, $G_z$, and phase-encoding gradients, $G_{x,y}$.

The APGSTE-RARE experiment 42 was conducted with the following parameter settings: duration of the hard 90° excitation and 180° refocusing r.f. pulses were 6 μs and 12 μs, respectively. The number of echoes acquired in each echo train was $N_{RF}$=8 with $t_e$=4.2 ms.

Two different spatially-resolved propagators were acquired with different observation times Δ, namely Δ=150 ms and Δ=900 ms. The imposed interstitial flow velocity $v_i$ was scaled as the inverse of observation time, so that the total interstitial displacement $v_i$Δ was identical for the two experiments and the effects of self-diffusion could be observed. For the observation time of 150 ms, a fluid flow rate of 0.03 ml min$^{-1}$ ($v_i$=91±3 ft day$^{-1}$ (0.32±0.01 mm s$^{-1}$)) was imposed, hence the experiment with an observation time of 900 ms was performed at a flow rate of 0.005 ml min$^{-1}$ ($v_i$=15±1 ft day$^{-1}$ (0.05±0.003 mm s$^{-1}$)).

Displacement encoding was achieved by two pairs of bipolar gradients g of duration of δ/2=0.14 ms and maximum amplitude of g=2.8 T m$^{-1}$ for Δ=150 ms and g=1.3 T m$^{-1}$ for Δ=900 ms.

The 3D spatially-resolved propagators were acquired with a FOV of 13.5 mm×4.5 mm×4.5 mm and 144 voxels×48 voxels×48 voxels in the frequency-(z) and both phase-encoding directions (x and y), respectively, yielding 3D images with an isotropic resolution of 93.8 μm. In q-space, 65 points were acquired, leading to a FOV in the displacement direction of 1.0 mm. The displacement direction was chosen to be parallel to the superficial flow direction (z).

For a 3D spatially-resolved propagator experiment, a 3D q-$k_{phase}$-space under-sampling pattern is required. Thus, the shape of the probability density function (pdf) describing the under-sampling pattern was generated based on (1) the μCT-VDS approach for 2D $k_{phase}$-space and (2) the shape of 1D q-space derived from a spatially-unresolved propagator experiment. The two pdfs were multiplied to obtain a 3D probability distribution function, on the basis of which a sampling pattern was generated at a sampling fraction of 0.25.

Using $t_{RD}$=2 s and acquiring 16 signal averages at a sampling fraction of 0.25 of k,q-space, the acquisition time of the spatially-resolved propagators was 4 days for the Δ=150 ms experiment and 5 days for the Δ=900 ms experiment. This is 32 times faster than a fully sampled, simple spin-echo MRI experiment at the given signal-to-noise ratio.

The sample remained in the same position for both the velocity map and spatially-resolved propagator experiments.

Example 3—Image Processing

CS reconstructions were carried out using an add-on MATLAB toolbox, specifically, Object Oriented Mathematics for Inverse Problems (OOMFIP) (Benning et al. "Phase reconstruction from velocity-encoded MRI measurements—A survey of sparsity-promoting variational approaches" *J. Magn. Reson.* 238: 26-43; 2014).

Individual under-sampled k-space datasets under flow and stationary conditions were reconstructed separately to yield complex-valued MRI images. The velocity maps were then calculated from these phase maps using standard procedures. Phase maps were calculated for the odd and even echoes separately, and the resulting phase difference maps of odd and even echoes were recombined by voxel-wise averaging for improved accuracy of the velocity maps. The magnitude images of the stationary MRI datasets were then averaged to generate a binary mask which was multiplied by the velocity maps to null the background noise in the velocity maps.

Figure 5A:
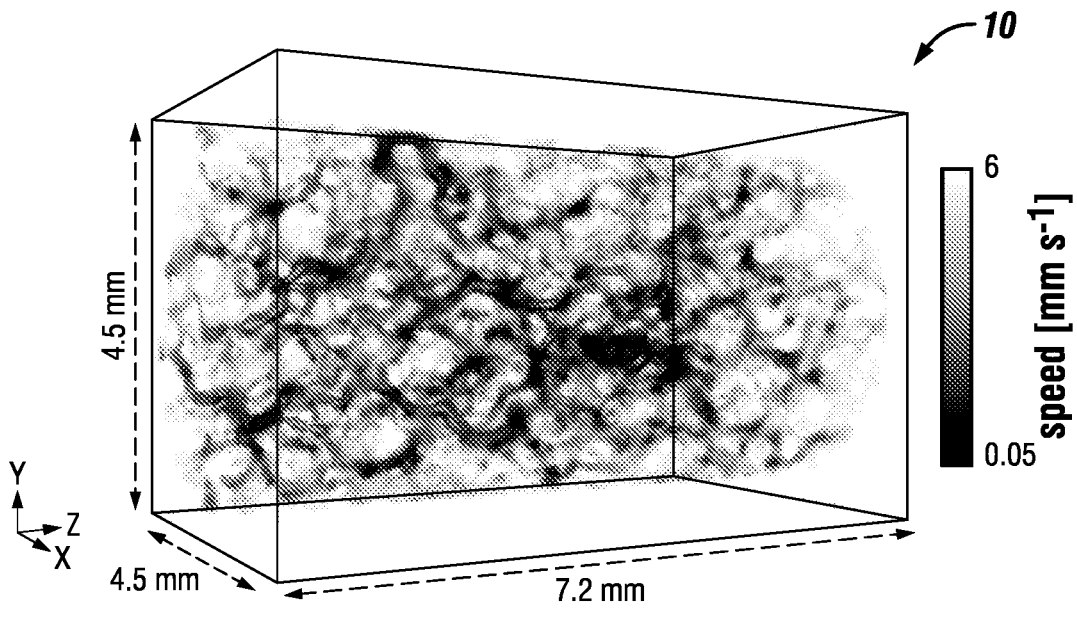
FIG. 5A is a pore-scale 3D magnitude flow map illustrating the main flow channels through the Ketton rock sample in the non-limiting example of the present invention.

FIG. 5A is a pore-scale 3D magnitude flow map showing the main flow channels through the Ketton rock sample. The map was generated from the combined x-, y-, and z-velocity components for the flow of water in the Ketton sample at the imposed flow velocity of $v_i$=91±3 ft day$^{-1}$ (0.32±0.01 mm s$^{-1}$). Velocity distributions of the z- and y-velocity components are illustrated graphically in FIGS. 5B and 5C, respectively. The x-velocity component has a similar distribution of velocities to the y-velocity component.

By visually inspecting the flow map of FIG. 5A, two characteristics are observed. First, it is seen that most water in the pore space of the rock sample has low mobility with a typical speed <0.2 mm s$^{-1}$. Nearly 70% of the voxels in this region of the rock contain fluid flow with lower speed than the mean absolute flow speed of approximately 0.5 mm s$^{-1}$. Second, the flow is heterogenous and is concentrated in a few high-velocity flow channels.

Figure 5B:
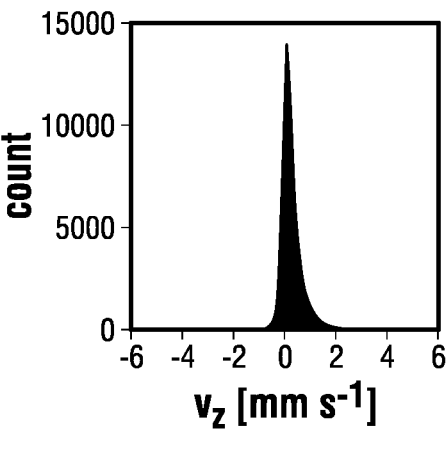
FIGS. 5B and 5C are graphical velocity distributions of the z- and y-velocity components, respectively.
Figure 5C:
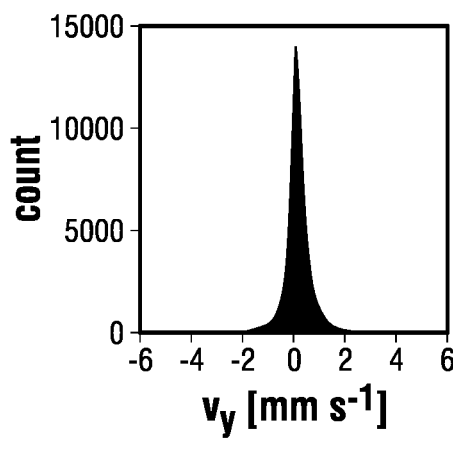

As determined from FIGS. 5B and 5C, the distribution of $v_z$ exhibits a long positive tail, a significant intensity at $v_z$=0 mm s$^{-1}$ which represents stagnant water, and a considerable amount of negative flow or backflow, represented by negative velocities. The long positive tail illustrates the heterogeneity in the flow through the rock sample with the highest velocities extending to ~50 times the modal velocity of $v_z$~0.08 mm s$^{-1}$. The mean velocity along the superficial flow direction (z) was calculated to be $v_z$=0.32 mm s$^{-1}$ (91 ft day$^{-1}$), which is in an excellent agreement with the imposed interstitial flow velocity in the macropores. The distribution of $v_y$ is symmetrically distributed around $v_y=0$ mm s$^{-1}$ (i.e., zero net flow) with velocities up to $v_y\sim\pm2$ mm s$^{-1}$. It was found that the positive and negative parts of the distribution of $v_y$ are described well by a single-exponential function.

Example 4—Direct Flow Simulation

Two LBM algorithms were used to simulate single-phase flow in rocks. For the Ketton sample, the fluid flow was computed using an energy-based LBM (eLBM) simulator that utilises the multiple-relaxation-time (MRT) model as a momentum-balance solver. eLBM was run in single-phase mode by initializing the pore-space with a single-phase fluid and injecting the same phase at the inlet. Therefore, a diffuse interface does not emerge in the simulations. In other words, eLBM could be seen as MRT-LBM with constant velocity inlet and gradient-free outlet boundary conditions.

For the Estaillades sample, the flow was simulated using an MRT-LBM algorithm based on the same MRT solver.

Simulations were performed on images with a size of 1671 voxels×643 voxels×643 voxels (in the z, x, and y directions) at an isotropic spatial resolution of 7.0 μm for Ketton, and 4279 voxels×1500 voxels×1500 voxels (in the z, x, and y directions) at an isotropic spatial resolution of 3.0 μm for Estaillades.

In order to be able to quantitatively compare the LBM and MRI velocity data, the velocities of the high-resolution LBM simulations were scaled such that the mean slice-by-slice flowrate of the LBM simulations was equal to the imposed flowrate of 0.03 ml min$^{-1}$. The flowrate for each slice was calculated by multiplying the sum of all velocities within the slice with the area of each voxel. In the case of Estaillades, the high-resolution simulation data were first coarse-grained (Lanczos filter) to 6.0 μm spatial resolution for more efficient image registration and data manipulation. For all quantitative analysis, the simulated data were down-sampled to 35 μm spatial resolution (Lanczos filter) to enable direct comparison with the acquired MRI velocity data.

Example 5—Co-Registering

The direct flow simulation image and the velocity map of flow through the rock acquired in the superficial flow direction (z) were co-registered in AVIZO™ using the "Register Images" module.

The aim of the image co-registration was to spatially align MRI velocity maps and μCT-based LBM simulations in order to be able to qualitatively and quantitatively compare the flow fields of both methods. MRI intensity images, obtained by calculating the magnitude of complex-valued stationary MRI datasets, and μCT grayscale intensity images, used to generate the pore space for simulations, were used as inputs for image registration.

First, the μCT intensity image (model image) was manually pre-aligned with the MRI intensity image (reference image). Next, the alignment of the model image relative to the reference image was optimised using rigid transformations with the normalised mutual information (Pluim et al. "Mutual-Information-Based Registration of Medical Images: A Survey" *IEEE T Med Imaging* 22: 986-1004; 2003 and Studholme et al. "An overlap invariant entropy measure of 3D medical image alignment" *Pattern Recognit* 32: 71-86; 1999) as a metric for the goodness of image alignment. In the optimisation procedure, the data were down-sampled, and the image registration was performed in steps at increasing spatial resolutions for more efficient image registration. Extensive direction and Quasi Newton optimizers were used for the co-registration of the coarse-resolution and the finest-resolution images, respectively. After the image co-registration process was completed, the resulting transformation of the μCT intensity image was applied to the LBM simulation.

The co-registered μCT intensity image and LBM simulation were resampled onto the MRI data coordinate system using a Lanczos filter to enable the MRI flow maps and μCT-based images, including LBM simulations, to be visualised and compared on the same grid.

FIGS. 6A-6C provide a visual comparison of 2D (xy) image slices extracted from the LBM simulation and the co-registered image for the Ketton rock sample. FIG. 6A was extracted from the 3D high-resolution LBM simulation at 7 μm spatial resolution, while FIG. 6B was extracted from the co-registered 3D image at 35 μm spatial resolution. The images shown in FIGS. 6A-6C represent the velocity component in the superficial flow direction (z). Good agreement is observed between the LBM simulation and MRI velocity data. Essentially all characteristics of the flow behaviour present in the MRI flow maps in Ketton are reproduced by the LBM simulation. This includes the location of high-velocity flow channels and the occurrence and location of the regions with backflow (i.e., negative (z) velocities). As is evident from the difference map in FIG. 6C, the magnitude of simulated velocities is also in a good agreement with the acquired MRI velocities, although LBM seems to underestimate the magnitude of velocities in the high-velocity flow channels of the rock. This observation contradicts the results reported by Manz et al. ("Flow and dispersion in porous media: Lattice-Boltzmann and NMR studies" *AIChE J.* 45: 1845-1854; 1999) who reported that LBM overpredicts large velocities, which could be due to a different LBM code used to simulate flow. Standard deviation calculated from the middle section of the 3D difference flow map is 0.37 mm s$^{-1}$. Overall, both the simulated and MRI data show that the flow in Ketton rock is highly heterogeneous with the flow being carried by a few high-velocity flow channels.

To further investigate the agreement between the experimental and simulated flow data, more quantitative analysis was performed by comparing the velocity distributions and voxel-by-voxel velocities of the two datasets. FIG. 7 shows that both the simulated and experimental distributions of $v_z$ are significantly skewed and have a long positive tail, which extends far beyond the modal velocity of each distribution, and a considerable degree of backflow, which is represented by negative velocities. Overall, the positive velocities with values greater than $v_z\approx0.1$ mm s$^{-1}$ are well predicted by LBM. The experimental and simulated distributions also show that a significant amount of fluid in the pore space of Ketton is stagnant or near stagnant with velocities around $v_z=0$ mm s$^{-1}$. This observation is consistent with the visual inspection of velocity maps in FIGS. 6A-6C, where fluid in the majority of pores appears to be near stagnant.

However, there also are noticeable differences between the two velocity distributions. In terms of the shape of the distributions, the two main discrepancies are the location and population of the modal velocity peak and the distribution of backflow. Compared to the MRI velocity distribution with the modal velocity of $v_z\approx0.08$ mm s$^{-1}$, the modal velocity peak of the simulated dataset is located at a lower velocity of $v_z\approx0.02$ mm s$^{-1}$ and has significantly more voxels associated with it. MRI velocity measurements are, of course, affected by experimental noise. Although it was estimated that in this case the overall noise-related velocity errors are relatively small, i.e., on the order of 0.01 mm s$^{-1}$, relative to the measured velocities, larger noise-related errors can arise in the voxels at the edges of grains because of lower SNR due to partial volume effects. These errors in velocity measurement can significantly decrease the sharpness of the modal velocity peak and, in general, lead to broadening of the velocity distribution. Regarding backflow, the MRI dataset exhibits a greater degree of backflow which extends further than that predicted by LBM.

Voxel-by-voxel comparison between the simulated and experimental velocity maps is shown in FIG. 8. Overall, good agreement is observed between the two datasets, as most voxels lie close to the straight reference line (white dashed line) with a slope of unity. Significant differences between the MRI and simulated velocities are observed for a relatively small number of voxels (note the logarithmic scale of the gray-scale bar). FIG. 8 also shows that a number of voxels representing stagnant or near-stagnant liquid in the LBM simulation exhibit a range of positive and negative velocities significantly greater than $v_z$=0 mm s$^{-1}$ in the MRI velocity map. This can be partly explained by experimental noise, especially at the pore-grain interfaces where noise can compromise the accuracy of the measured velocities due to partial volume effects.

The experimental and simulated velocity data were further analysed using a pore-scale approach, wherein velocity information was obtained for each individual pore in the images and then compared between the two datasets. To achieve this, a (combined) binarized structural image was first generated from the individual binary masks of the MRI and LBM datasets by only selecting the voxels that are shared between the two datasets. This is done so that the same pores consisting of the same number of voxels can be later identified using pore labelling. The pore space of the structural image was then separated into individual, labelled pores using a Chamfer distance map and marker-based watershed algorithm in AVIZO™. The labelled structural image and each velocity dataset separately (MRI or LBM) were then used as inputs in the labelled pore analysis to extract and correlate the flow properties for individual pores.

The results of this analysis are shown in FIGS. 9A and 9B. FIG. 9A shows a pore-by-pore comparison between the simulated and experimental velocity data; the dashed line in the plot represents a reference line with a slope of unity. Although there is a good overall agreement between the two datasets, the general trend is that the LBM simulation slightly underpredicts large pore velocities, but overpredicts small and negative pore velocities; inspection of FIGS. 6A-6C and FIG. 8 also reveals a similar trend. This observation, however, cannot be fully explained by the experimental noise. A different view on the data is taken in FIG. 9B, where for both datasets the fraction of the total flow $(v_z^{sum}(i)/\Sigma v_z^{sum})$ is plotted as a function of the fraction of the number $(N_p(i)/\Sigma N_p)$ of those pores that carry this flow. As can be seen, agreement between experiment and LBM simulation is excellent. An interesting aspect of the data shown in FIG. 9B is the indication that the flow field in Ketton rock exhibits significant heterogeneity on the pore scale with 10% of the pores carrying ≈50% of the flow. These results are consistent with the visual inspection of velocity fields in FIGS. 6A-6C.

Within the micropores of Ketton, the information about the imbibed fluids was difficult to capture by MRI due to the short $T_2$ relaxation times. In water-saturated Estaillades, this information can be captured more easily due to the longer $T_2$ relaxation times. To illustrate both the fluid-saturated microporous and macroporous regions in the Estaillades rock, the magnetic resonance intensity image, generated from the complex-valued MRI data, was co-registered with the μCT data of the rock; 2D (xy) slice image of the co-registered MRI and μCT dataset is shown in FIG. 10, where the color-coded MR signal intensities represent water concentration in the micropores and macropores, respectively. FIG. 10 shows that microporosity occupies large regions of the rock, whereas only a few macropores can be identified in the rock structure, which are likely to carry most of the flow through the rock. It can also be seen that no water is present within the dense calcitic grains of the Estaillades formation.

Figures 11A, 11D, 11G:
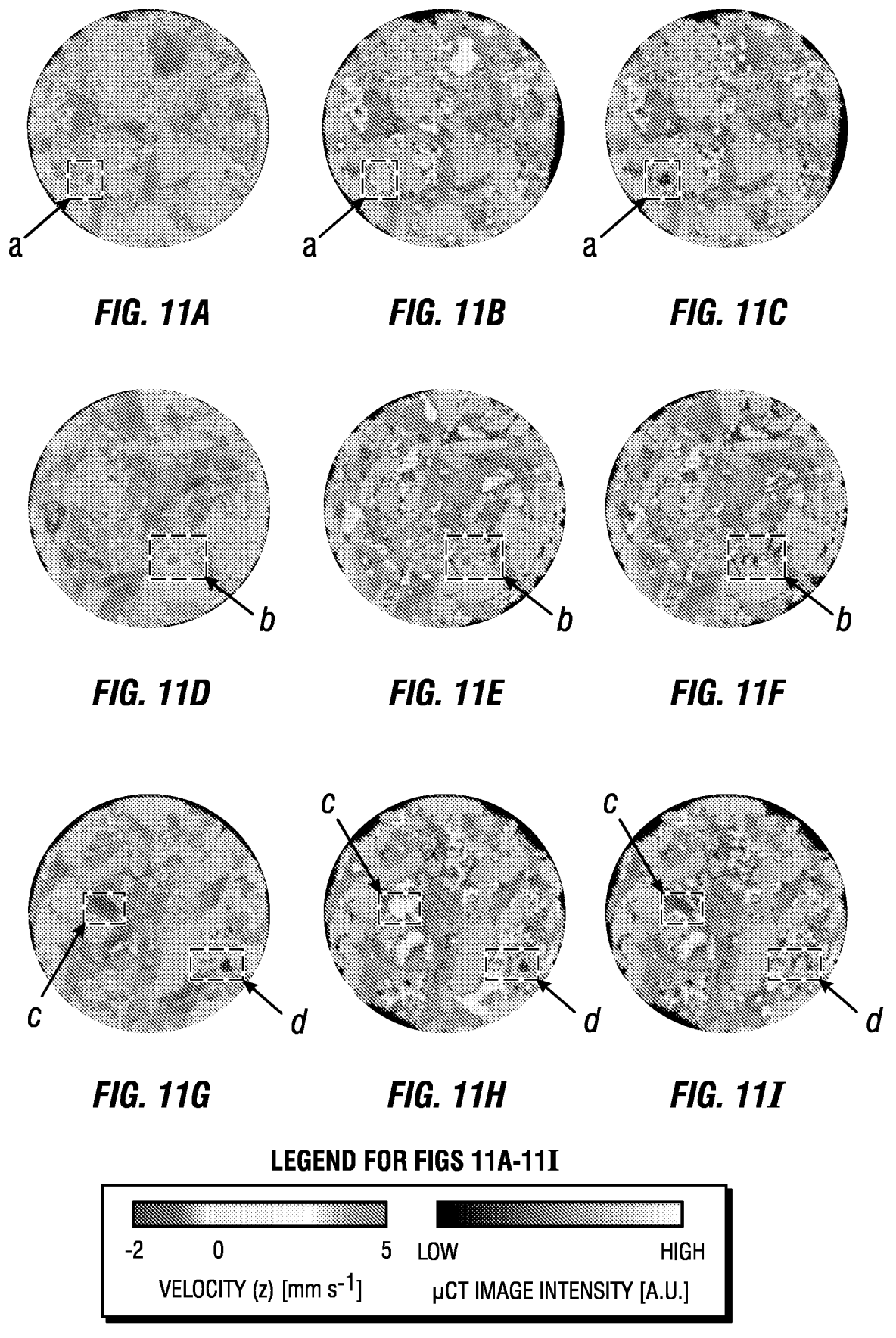

FIGS. 11A-11I provide a visual comparison between the LBM simulation and MRI velocity map for Estaillades. Three different 2D slice images extracted from the co-registered MRI and μCT dataset are shown, representing the velocity component in the superficial flow direction (z). FIGS. 11A, 11D and 11G show 2D (xy) slice images of Estaillades obtained from the 3D LBM simulation at 6 μm spatial resolution, while FIGS. 11B, 11E and 11H show co-registered images at 35 μm spatial resolution. The difference map $(v_z(\text{MRI})–v_z(\text{LBM}))$ was obtained by calculating the absolute difference between the coarse-grained LBM simulation and MRI flow map. Three regions outlined with dashed boxes and labelled as regions a, b, c and d identify interesting flow patterns in the rock sample.

Considering the complex structure of the Estaillades formation, good qualitative agreement is observed (ignoring microporous regions) between the three image slices of the LBM and MRI datasets, with some local deviations in some of the pores. Similar to Ketton, it can be seen in both LBM and MRI data that the flow in Estaillades is highly heterogenous with a few high-velocity flow channels. MRI flow maps also reveal that the fluid is stagnant or near-stagnant in the microporous regions of the rock (i.e., dark grey μCT image intensities). Region 'a' (shown in FIGS. 11A, 11B and 11C) represents a large pore where the LBM predicts the formation of a high velocity flow channel with $v_z \gtrsim 5$ mms$^{-1}$ and a diameter extending to about half of the width of the pore, whereas MRI velocity map shows lower velocities in the same pore. Interestingly, the acquired MRI velocity map indicates that two relatively small high-velocity channels have formed in region 'a', instead of one, as predicted by LBM. In the other large pores in this image slice with significant flow, LBM tends to underestimate the flow velocity, as is evident from the difference map (FIG. 11C).

Region 'b' (shown in FIGS. 11D, 11E and 11F) shows another high-velocity flow channel in the middle of a relatively large pore. In this case, the LBM has accurately predicted the location and velocity of the flow field.

In region 'c', illustrated in FIGS. 11G, 11H and 11I, a microporous rock grain can be seen. No flow information was obtained from this region using the LBM simulation, because the pore size was below the imaging resolution of X-ray μCT. However, using MRI, the average flow velocity can be accurately measured at voxel sizes much greater than the pore size of the fluid-saturated rocks. In this case, the MRI flow map indicates that the microporous grain contains stagnant or near stagnant fluid.

Lastly, region 'd', also illustrated in FIGS. 11G, 11H and 11I, shows a complex flow behaviour with adjacent positive and negative flow channels in a large macropore. This complex flow behaviour has been relatively accurately predicted by LBM, as good qualitative agreement in this region is observed between the MRI and LBM velocity data.

Visual inspection of FIGS. 11A-11I reveal that, while complex flow patterns are predicted well by LBM for some pores, significant differences between MRI and LBM data can be seen for other pores.

To investigate these discrepancies in more detail, a more quantitative analysis similar to that carried out for Ketton was performed on a pore-by-pore basis. This analysis was carried out for the macroporous regions of the rock that are shared between the binarized structural images of the MRI and LBM datasets. The results of this analysis are shown in FIGS. 12A and 12B. This analysis resulted in a large number of small pores, consisting of a few voxels. Hence, for clarity, only pores with a radius greater than 35 μm are shown. FIG. 12A shows that there is a much greater scatter of the points and deviation from the reference line of slope unity relative the data observed for Ketton (FIG. 9A). However, as with the Ketton data, the LBM simulation generally underestimates large pore velocities, but overestimates negative pore velocities. As can be seen in FIG. 12A, there is a large number of pores in the MRI velocity map with significant negative and positive mean pore z-velocities, $v_z^m$, which have $v_z^m \sim 0$ mm s$^{-1}$ in the LBM simulation. A close inspection of the LBM simulation shown in FIGS. 11A-11I also reveals a similar trend as the LBM simulation predicts more highly localised flow than is seen in the MRI velocity data. This observation is also supported by the plot shown in FIG. 12B, where, based on the LBM data, approximately 94% of the flow in the Estaillades rock is carried by just 10% of the pores. Similarly, data extracted from the acquired MRI velocity map indicate that the flow through the macroporous regions of the rock is highly heterogeneous with 10% of the pores carrying ≈80% of the flow. Compared to Ketton, where 50% of the flow was carried by 10% of the pores, 60% more flow is passing through the same percentage of pores in the Estaillades formation which is an indication of its highly heterogeneous rock microstructure.

The qualitative analysis of FIGS. 11A-11I indicated that the fluid-saturated micropores mainly exhibit low flow velocities. However, as is evident from FIG. 10, microporosity occupies large proportion of the total porosity in Estaillades. In fact, microporosity can constitute more than half of the total rock porosity in the Estaillades rock. To investigate the extent to which these fluid-saturated micropores, which occupy significant portion of the total porosity, affect the global flow rate, quantitative analysis was performed on the MRI velocity map with velocities encoded in the superficial flow direction (z). For this analysis, the flowrate, $Q_z$, for each axial (xy) image slice was calculated by summing the z-velocities of each voxel within a given slice and then multiplying by the cross-sectional area of a single voxel. This analysis was performed for three separate images, namely the total porosity image, the macroporosity image, and the microporosity image. To generate an accurate value of $Q_z$ for each image slice, the velocity map was first multiplied by two masks, which were generated by manual thresholding of the MRI intensity image (FIG. 10).

The first mask is needed to null the background noise and to separate the macroporous regions and the microporous regions; in the context of this analysis, the macroporous regions are defined as the regions with large and medium-sized pores that are coloured in green in FIG. 10 (i.e., ~the pores that can be captured by μCT, as shown in FIGS. 11A-11I), but the microporous regions, in the context of this study, are defined as regions with pore sizes well below image resolution—these are coloured in blue in FIG. 10.

The second mask, which is computed by averaging multiple binary masks at different threshold values, is required to account for the partial volume effects and the fact that the majority of voxels are only partially saturated by water in order to make an accurate estimate of $Q_z$. The plot of $Q_z$ as a function of the position of the image slices for the three different porosity images in the middle region of the rock is shown in FIG. 13, which depicts total porosity 72, macroporosity 74, and microporosity 76 of the rock. The dashed line represents the flowrate, which was imposed during MRI experiments, i.e., at $Q_z$=0.03 ml min$^{-1}$.

It can be seen that although most of the flow goes through macropores, the microporous regions also noticeably contribute to the total flowrate through the Estaillades plug. For example, for the region of the rock from ~0.5 to 1.3 mm along the z-direction, the macroporous and microporous regions have approximately the same contribution to the total flow through the rock. The average contribution of microporosity to flow in this region of the rock was estimated to be 36±5% relative to the average total $Q_z$ (the uncertainty was estimated by varying the manual segmentation threshold value by ±10% relative to the chosen threshold).

Note that in MRI velocity image of Ketton, the macropore network alone (as shown in FIG. 6A-6C) accounted for the total $Q_z$ in the rock, so the contribution of micropores to the flow is expected to be minor. This example indicates that microporosity plays an important role in the fluid flow and transport processes in microporous carbonate rocks.

The method may be performed in any order, and repeated as desired. Part or all of the method may be performed.

While the embodiments are described with reference to various implementations and exploitations, it will be understood that these embodiments are illustrative and that the scope of the inventive subject matter is not limited to them. Many variations, modifications, additions and improvements are possible. For example, one or more image may be performed using one or more of the techniques herein. Various combinations of the techniques provided herein may be used.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

We claim:

1. A method for calibrating a direct flow simulation of a rock sample, the method comprising the steps of:

providing a 3D image of a rock sample, wherein the 3D image is comprised of a plurality of voxels;

generating a segmented structural image of the rock sample from the 3D image by selecting each of the plurality of voxels to represent either a pore space or a solid material;

simulating fluid flow on the segmented structural image with a direct flow simulation;

generating a 3D spatially-resolved fluid velocity map for one or more fluid phases at a pore-scale resolution using pulsed field gradient nuclear magnetic resonance imaging using compressed sensing to reconstruct spatially-resolved fluid-flow encoded phase difference maps for each of the one or more fluid phases under flowing and stationary conditions, calculating a flow velocity map for each of the fluid phases, and subtracting the phase difference measured under stationary conditions from the phase difference measured under flowing conditions; and comparing the simulated fluid flow and the 3D spatially-resolved fluid velocity map to correlate a pore structure of the rock sample with fluid flow in the pores;

thereby calibrating the direct flow simulation across the rock sample.

2. The method of claim 1, wherein the comparing step comprises co-registering the simulated fluid flow and the 3D spatially-resolved fluid velocity map.

3. The method of claim 1, wherein the direct flow simulation is based on a lattice Boltzmann method.

4. The method of claim 1, wherein the pulsed field gradient nuclear magnetic resonance is combined with a RARE MRI pulse sequence.

5. The method of claim 1, wherein the step of spatially-resolving fluid flow is performed by velocity mapping to provide an average velocity of fluid flow for each voxel within the 3D image.

6. The method of claim 5, wherein the velocity mapping is performed with a pulsed gradient spin echo sequence in combination with an MRI pulse sequence.

7. The method of claim 6, wherein the MRI pulse sequence is a RARE MRI pulse sequence.

8. The method of claim 1, wherein the step of spatially-resolving fluid flow is performed using a spatially-resolved displacement propagator to provide a distribution of fluid flow for a predetermined time for each voxel within the 3D image.

9. The method of claim 8, wherein the spatially-resolved displacement propagator is acquired by an alternating pulsed gradient stimulated echo sequence in combination with an MRI pulse sequence.

10. The method of claim 9, wherein the MRI sequence is a RARE MRI pulse sequence.

11. The method of claim 1, wherein the 3D image of the rock is obtained by X-ray computed tomography.

12. The method of claim 1, wherein the step of comparing the simulated fluid flow and the 3D spatially-resolved fluid velocity map includes quantifying a contribution of microporosity in the rock sample to fluid flow.

13. The method of claim 1, wherein the calibrated direct flow simulation is used for making a decision with respect to recovery of hydrocarbons from the subterranean formation.

14. The method of claim 1, wherein the calibrated direct flow simulation is used for making a decision with respect to carbon capture and sequestration in the subsurface formation.

15. The method of claim 1, wherein the calibrated direct flow simulation is used for making a decision with respect to a geothermal heat extraction process.

* * * * *